United States Patent [19]

Okarma et al.

[11] Patent Number: 4,963,265

[45] Date of Patent: Oct. 16, 1990

[54] PLASMA PROCESSING DEVICE WITH ANAPHYLATOXIN REMOVER

[75] Inventors: Thomas B. Okarma, Palo Alto; Brian R. Clark, Redwood City; L. Bernard Lerch, Menlo Park; Chin-Hai Chang, Los Altos, all of Calif.

[73] Assignee: Applied ImmuneSciences, Inc., Menlo Park, Calif.

[21] Appl. No.: 191,039

[22] Filed: May 6, 1988

[51] Int. Cl.⁵ .................. B01D 39/00; B01D 61/58; B01D 15/08
[52] U.S. Cl. ..................... 210/638; 210/646; 210/651; 210/691; 210/502.1; 210/908; 604/5; 604/6
[58] Field of Search ............ 210/634, 635, 638, 645, 210/646, 651, 660, 691, 321.72–321.9, 502.1, 908; 604/4, 5, 6; 530/380, 412; 424/101; 502/407, 410

[56] References Cited

U.S. PATENT DOCUMENTS

| | | | |
|---|---|---|---|
| Re. 31,688 | 9/1984 | Popovich et al. | 210/651 |
| 3,742,946 | 7/1973 | Grossman | 210/321.87 |
| 3,998,946 | 12/1976 | Condie et al. | 424/101 |
| 4,081,431 | 3/1978 | Stephan et al. | 424/101 |
| 4,086,924 | 5/1978 | Latham, Jr. | 604/6 |
| 4,103,685 | 8/1978 | Lupien et al. | 604/6 |
| 4,170,590 | 10/1979 | Stephen et al. | 530/380 |
| 4,212,738 | 7/1980 | Henne | 210/321.75 |
| 4,223,672 | 9/1980 | Terman et al. | 604/5 |
| 4,267,047 | 5/1981 | Henne et al. | 210/500.25 |
| 4,272,523 | 6/1981 | Kotitschke et al. | 530/380 |
| 4,276,172 | 6/1981 | Henne et al. | 210/500.24 |
| 4,362,155 | 12/1982 | Skarkovich | 604/6 |
| 4,428,744 | 1/1984 | Edelson | 604/6 |
| 4,464,165 | 8/1984 | Pollard, Jr. | 210/635 |
| 4,512,897 | 4/1985 | Crowder, III et al. | 210/656 |
| 4,540,401 | 9/1985 | Marten | 604/28 |
| 4,610,791 | 9/1986 | Henne et al. | 210/500.23 |
| 4,614,513 | 9/1986 | Bensinger | 210/651 |
| 4,627,915 | 12/1986 | Kuroda et al. | 210/195.2 |
| 4,693,985 | 9/1987 | Degen et al. | 210/502.1 |
| 4,814,083 | 3/1989 | Ford et al. | 210/490 |

*Primary Examiner*—W. Gary Jones
*Attorney, Agent, or Firm*—Bertram I. Rowland

[57] ABSTRACT

Blood derived fluids are subjected to modification resulting in the production of anaphylatoxins. The anaphylatoxins may then be removed by passing the modified blood through silicic acid particles in an amount sufficient to substantially reduce the anaphylatoxins, while still retaining the other blood components and without affecting adversely the use of the blood for the patient.

8 Claims, 4 Drawing Sheets

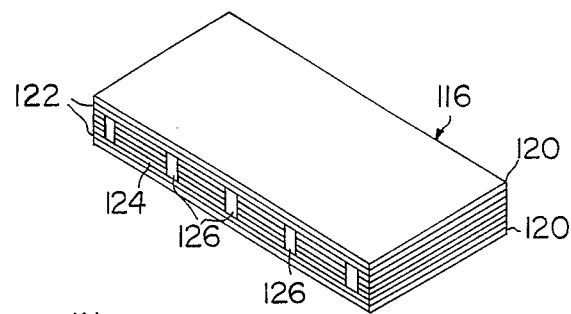
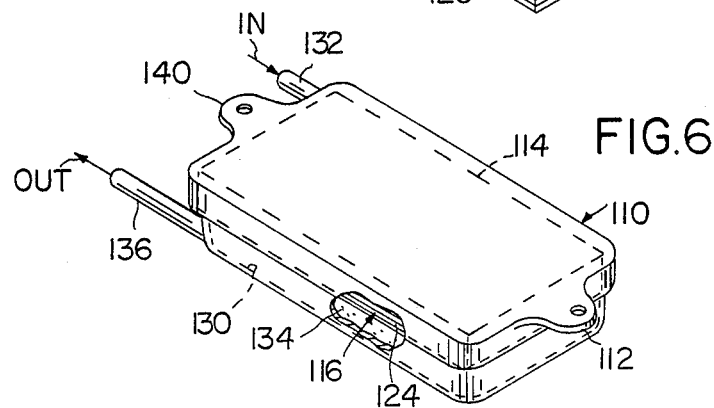
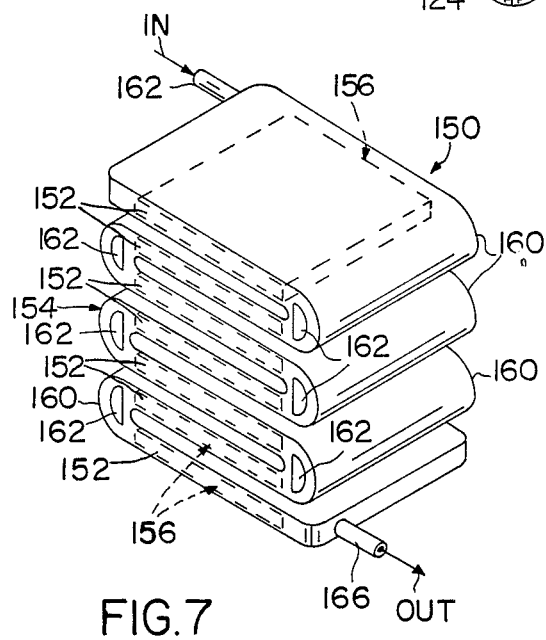
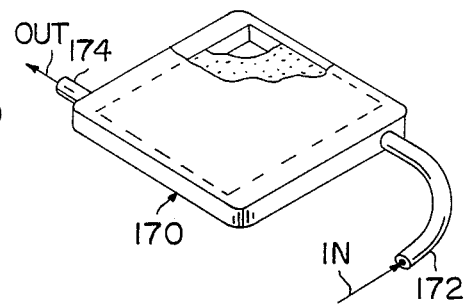

PLASMA PROCESSING DEVICE WITH ANAPHYLATOXIN REMOVER

TECHNICAL FIELD

The subject invention is concerned with plasma processing devices involving separation of soluble plasma components.

BACKGROUND

The blood system is the highway of the body providing for transfer of materials, passage of cells, removal of debris, protection against disease and monitoring of bodily functions. In conjunction with other organs such as the liver and kidney, the body is cleansed of many deleterious substances and a homeostasis is maintained. In addition, the lymphocytic system acts to protect the body from invading organisms and foreign substances, by ingestion, lysis, coating, as well as other mechanisms.

In many situations, the host produces substances which enter the blood and which are deleterious to the host. Such situations include autoimmune diseases, septic shock, immune complex formation, and the like. In instances of kidney failure, kidney dialysis is required in order to maintain the proper level of salts and other components in the host.

Various devices have been developed and are being developed to separate components of the blood extracorporeally. In these situations, the method of separation may result in activation of processes which produce undesirable products. When the plasma is returned to the patient, who is normally in a physically weakened state, the presence of these deleterious substances can be quite harmful.

It is therefore of great interest to develop ways to be able to treat blood extracorporeally, while preventing the formation of undesirable substances or, in the alternative, selectively removing the undesirable substances, while retaining the desirable components in the blood for return to the host.

RELEVANT LITERATURE

Descriptions of blood component removal systems may be found in U.S. Pat. Nos. 4,086,924; 4,103,685; 4,223,672; 4,362,155; 4,428,744; 4,464,165; 4,540,401; 4,614,513; 4,627,915 and Re 31,688 and EPA 0 082 345. References associated with complement activation include Breillatt and Dorson, *ASAIO J.* (1984) 7:57–63 and McLeod et al., *Artif. Organs* (1983) 7:443–449. U.S. Pat. No. 3,742,946 describes the use of charcoal to remove salicylates and barbituates from plasma or serum.

SUMMARY OF THE INVENTION

Methods and devices are provided for treating blood samples in a first stage involving complex formation on a solid surface, resulting in the formation of anaphylatoxins and transferring the effluent from the first treatment chamber to a second chamber containing silicic acid for removal of anaphylatoxins and harvesting the isolate for further use. Particularly, dialysis, plasmapheresis, plasma composition remodeling, or affinity extraction devices may be joined to the anaphylatoxin remover, where the effluent from the anaphylatoxin removal chamber may be returned to a host free of injurious amounts of anaphylatoxins.

BRIEF DESCRIPTION OF THE DRAWINGS

FIG. 5 is a perspective view of a membrane stack;

FIG. 6 is a diagrammatic view of a device incorporating the membrane stack of FIG. 5;

FIG. 7 is a perspective view of a folded bag device; and

FIG. 8 is a perspective view of a silicic acid filter for attachment useful with the device of FIG. 6.

DESCRIPTION OF THE SPECIFIC EMBODIMENTS

Figure 1:
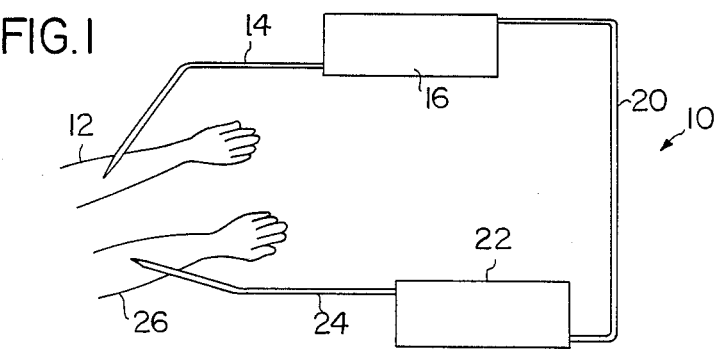
FIG. 1 is a diagrammatic view of a device according to this invention.

Methods and devices are provided for treating whole blood, plasma or serum in a first stage involving complex formation between specific binding pair members and then transferring the treated fluid to a second stage for removal of any anaphylatoxins with silicic acid. A blood stream, which may have been pretreated, and will usually be used as plasma or serum, that is, free of most cells, will be introduced into a first treatment chamber, where one or more components of the blood stream will be removed or remodeled, by increasing or decreasing concentrations of such components or changing ratios of components. Usually, the first chamber will comprise a dialysis membrane or a solid substrate to which may be bound one or more specific binding pair members. These specific binding pair members will be either ligands or receptors which bind to a reciprocal or homologous binding pair member. By passing the blood stream through the chamber, one or more components of the blood stream will be separated either by dialysis or by binding to the specific binding pair member. Normally, as a result of the presence of the complex and/or the nature of the solid support, anaphylatoxins, members of the complement cascade, are produced which can result in adverse responses when fluid containing the anaphylatoxins is returned to the host. These anaphylatoxins are for the most part $C_{3a}$, $C_{4a}$, $C_{5a}$ and their des arg analogs.

The first chamber may be used for a variety of purposes. In particular, members of a specific binding pair homologous to a component of interest may be employed to reduce the level of the component in the blood derived fluid. For example, immune complexes may be removed or remodeled by employing Protein A or other similar protein, e.g antibodies, specific for a constant region of immunoglobulins. Antibodies specific for DNA or other native host substances may be removed by binding the native substance to the surface. In other situations, one may wish to extract particular cell type proteins, such as tumor necrosis factor, or other factors associated with disease or treatment of the human host. Also, where a particular compound is present at an elevated level, the compound(s) level in the blood may be reduced.

For a number of reasons, membranes will normally be used which will allow for flow of the stream through the membranes, while providing for a high surface area, where a high density of the specific binding pair member may be achieved. Other means may be employed, such as plastic surfaces, e.g. polystyrene beads, hollow fibers, etc., where the surfaces may be functionalized.

Various membranes may be employed of a variety of materials, all of which to varying degrees encourage the formation of anaphylatoxins. Membranes may be prepared from nitrocellulose, cellulose, nylon, polypropylene, polyethylene, silicone, polycarbonate, polyester, polyterephthalate, etc., or combinations thereof. Usually, the membrane will have pores in the range of about 1 to 500 $\mu$, more usually in the range of about 2.5 to 25 $\mu$. As will be described subsequently, a plurality of membrane layers will be employed, where the membrane layers will be separated, so as to allow for the relatively free flow of the plasma or serum through the membrane, while providing for a high surface area to ensure contact of the blood components with the bound component.

Depending upon the purpose of the device, the surface area may be varied widely. Usually, the first stage will have the surface area in the range of about 0.2 to 3 $m^2$, more usually in the range of about 0.3 to 2.5 $m^2$. So long as the fluid is substantially cell free, the rate of flow need not be affected by concerns with cell lysis. Flow rates will generally be in the range of about 0.001 to 0.2 L/min, more usually in the range of about 0.002 to 0.1 L/min. The blood derived fluid, after passage through the first chamber, will be directed to a second chamber which contains the silicic acid.

In referring to first and second chambers or compartments, it is merely intended to have a first region which involves the separation of one or more components from the blood derived stream, where when the desired level has been achieved for the component(s) of interest, the stream may then be directed to the anaphylatoxin separation chamber.

The anaphylatoxin separation chamber may be of any convenient shape or dimension, which will provide for separation of anaphylatoxins, so as to reduce their level to a non-toxic level. The chamber will normally involve silicic acid particles of a size in the range of 50 to 500 $\mu$. The silicic acid particles are further characterized by having a mildly acidic or neutral pH, generally in the range of about 3 to 7, usually of about 4 to 7, preferably 5 to 7. The pH may vary with the properties of the plasma, although for the most part, the same pH will be used for differing samples. The pore size will be selected so as to accommodate the anaphylatoxin proteins while not adversely affecting the other proteins of interest. For the most part, the pore size will be in the range of about 50 to 350 Å, preferably 50 to 200 Å, more preferably about 50 to 150 Å.

The particle size will vary depending upon the uniformity of size, the nature of the particle, pore size, required flow rate, and the like. With a substantially uniform particle size, the particle size will average in the range of about 50 to 400 $\mu$, more usually 50 to 300 $\mu$. The particles should provide for a high surface area for high efficiency. Desirably, the surface area is at least about 200 $m^2/g$, and may be as high as 500 $m^2/g$, usually about 200 to 400 $m^2/g$.

The subject process finds particular application for removal of proteins having a pI greater than about 7 and a molecular weight in the range of about 15 to 50 kD.

Conveniently, the silicic acid particles may be maintained between one or more screens of a pore size which precludes the migration of the silicic acid particles outside the chamber. Usually, the pore size of the screen will be of range of from about 10 to 100 $\mu$, more usually of from about 15 to 75 $\mu$. The pore size will be chosen so as not to impede flow and not to become clogged, yet restrict escape of the silicic acid particles from the chamber.

The size of the anaphylatoxin separation chamber will vary depending upon the volume to be treated and whether the entire device is a disposable device, to be used for one or a few treatments, with the same or different blood sources, or is to be a device which will be rechargeable or regenerable and used repetitively for an extended period of time. Conveniently, the silicic acid chamber will generally be of a size to accommodate silicic acid in the weight range of about 5 g to 1 Kg, more usually in the range of about 10 to 500 g. Flow rates through the chamber will be about the same as the flow rates in the previous chamber. The amount of silicic acid employed will generally be from about 10 to 100 g/L of fluid, preferably from about 15 to 50 g/L of fluid.

The chamber may be of any convenient shape which allows for efficient exposure of the blood derived stream to the silicic acid surface. Thus, the chamber may be a box, cylindrical tube, spiral, irregular shaped, or the like, and include baffles, separators, etc. The housing for the two compartments may be a rigid plastic box, flexible bag, may have separate chambers joined by a conduit, or the like.

In carrying out the process of this invention, usually whole blood will be separated into plasma using any of the conventional plasma separating machines, such as Cobe, IBM 2997, Fenwal Autopheresis, etc. The plasma stream is then directed to the first compartment for separation or modeling of one or more components of the stream. The process may be continuous or batch, depending upon the particular situation. The extracted fluid is then directed to the silicic acid compartment for the removal of the anaphylatoxins, while substantially retaining all of the other desirable plasma components. The plasma may then be removed from the silicic acid compartment, modified or augmented as desired, and then returned to the host.

The level of the individual anaphylatoxin in the plasma returned to the patient after treatment with the subject device will be $C_{3a}$, 0–300 ng/ml; $C_{4a}$, 0–300 ng/ml; and $C_{5a}$, 0–70 ng/ml (the ranges include the des arg analogs). Desirably, the range will not be greater than about the original level of anaphylatoxins in the plasma. Levels of anaphylatoxins resulting from the plasma processing treatment alone may be as high as 60 times the original or greater. For example, $C_{3a}$ may be as high as 20,000 ng/ml; $C_{4a}$, 12,000 ng/ml; and $C_{5a}$, 800 ng/ml. Generally, the levels will be at least doubled and may exceed 10 times the original level.

To further understand the subject invention, the drawings will now be considered. In FIG. 1, a schematic of the subject device is provided. The device 10 receives blood from one arm 12 of a patient through conduit 14. Conduit 14 introduces the blood into the first chamber 16, where one or more components may be exchanged, removed, or otherwise modified. The blood exits into conduit 20 and is directed by conduit 20 to anaphylatoxin removal chamber 22. The modified blood free of an undesirable level of anaphylatoxins is then directed through conduit 24 to the other arm 26 of the patient. In this manner, the blood has been modified in accordance with the needs of the patient and is returned to the patient free of elevated levels of anaphylatoxins to avoid potential shock.

Figure 2:
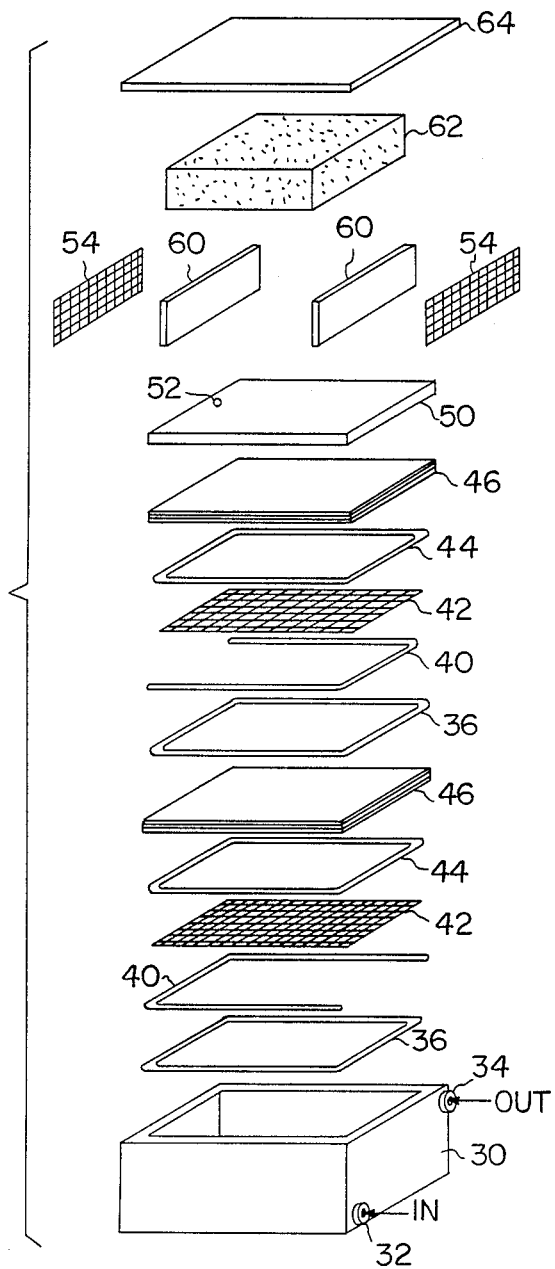
FIG. 2 is an exploded perspective view of a box device and its contents according to the invention.

In FIG. 2 is indicated an exploded view of a device in the shape of a box having first and second compartments where the first compartment has a plurality of membranes overlying one another and the second compartment has the silicic acid. The membrane compartment provides for an alternating direction of flow of the blood derived stream through the compartment. The device has a housing 30 with inlet 32 and outlet 34. Contained in the membrane compartment is O-ring 36, U-ring 40, and screen 42. The U-ring controls the direction of flow of the stream. On top of the screen 42 is a second O-ring 44 which separates the O-ring from membrane pack 46. The membrane pack will have a plurality of membranes lying one atop the other to which will be bound the specific binding pair members. Conveniently, each pack may contain from about 5 to 25, usually 5 to 20, membranes. The blood derived stream will pass up through the membrane pack 46 contacting the specific binding pair members and rising up through the pores to repetitively contact each succeeding membrane. Once the blood derived stream has passed through the membrane pack, the assemblage of O-ring 36, U-ring 40, positioned in the opposite direction of the previous U-ring 40, O-ring 36, screen 42, second O-ring 44 and membrane pack 46 may be repeated one or more times depending upon the size of the unit, the amount of material to be extracted, the binding capacity of the membrane packs and the like. The particular component which is the last component is not critical to this invention.

Various biocompatible materials may be employed for the various components. Conveniently, the O-ring and U-spacers may be high density polypropylene, the screens polypropylene and the housing polycarbonate.

Surmounting the components of the membrane compartment will be an inner lid 50 having port 52. The port 52 will be of approximately the same dimensions as the inlet and outlet ports 32 and 34 respectively of the housing 30. A polyethylene filter, not shown, conveniently of a pore size of 35–60 $\mu$ is applied across the port to prevent access of silicic acid particles into the membrane pack compartment. Barriers 54 and 60 are employed to maintain the silicic acid within a predetermined area in the silicic acid compartment. The silicic acid particles are indicated as a box 62. The silicic acid particles may be of a size in the range of from about 50 to 300 $\mu$. A cover 64 is then used to close the housing 30 completing the device.

Figure 3:
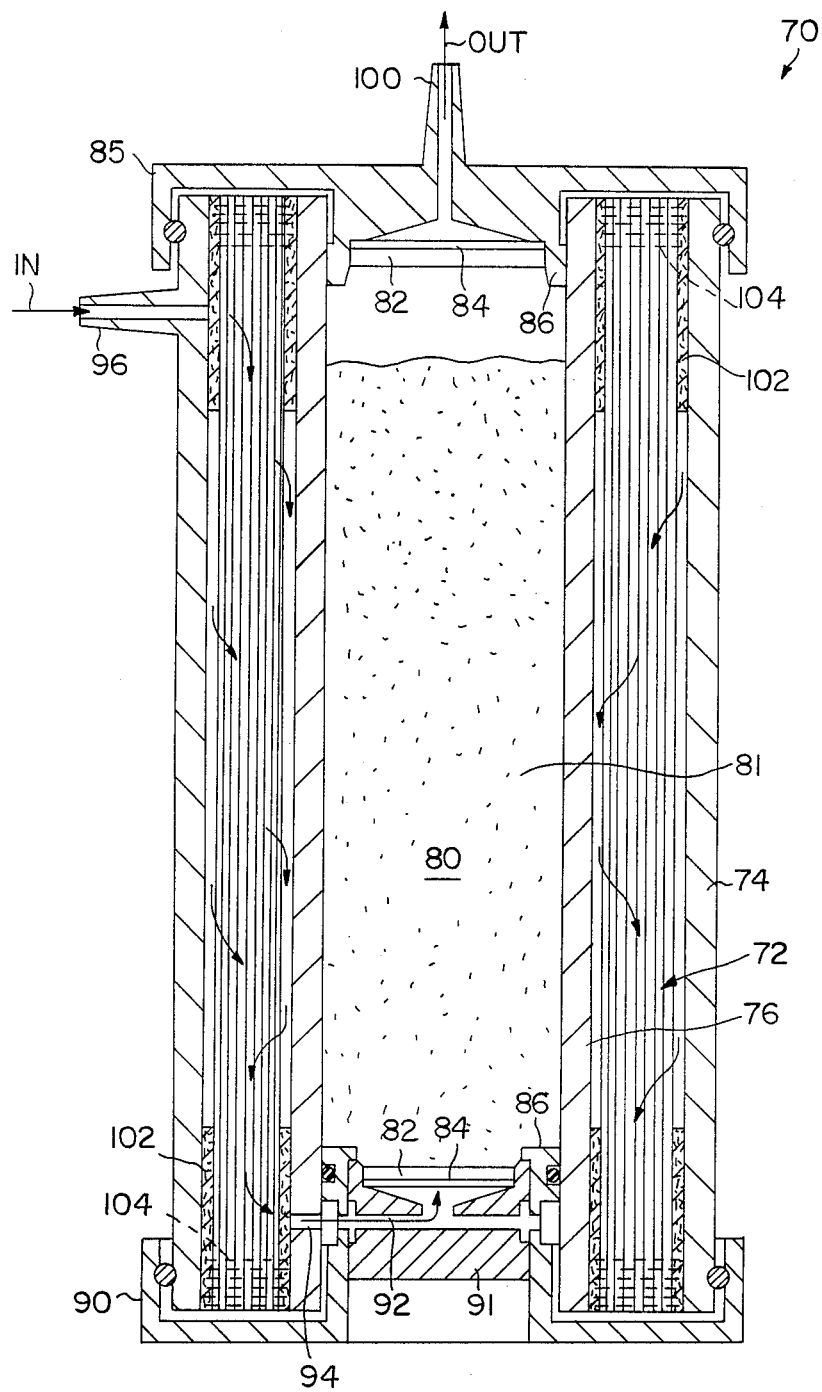
FIG. 3 is a cross-sectional elevation of a tubular device according to this invention.
Figure 4:
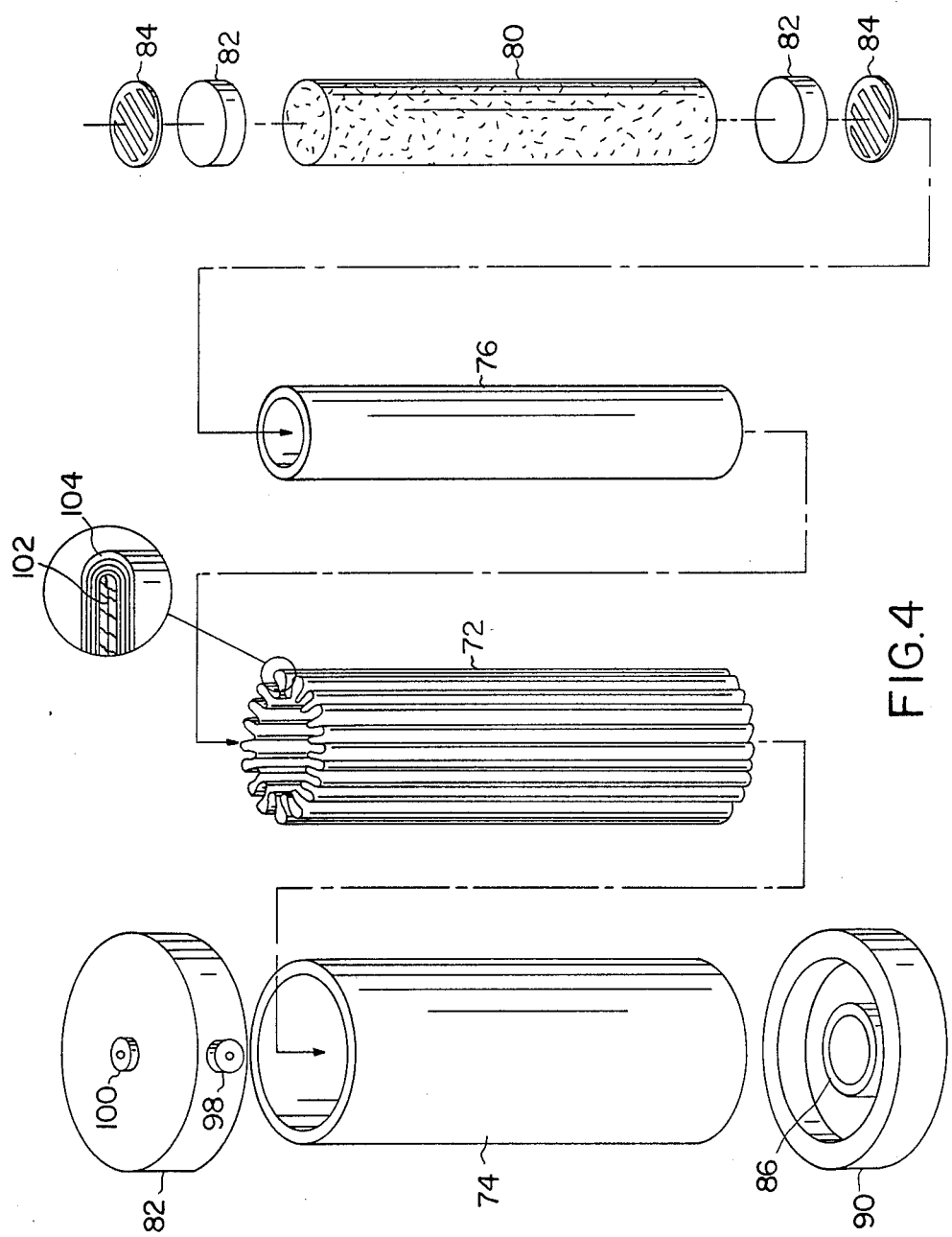
FIG. 4 is a perspective view of the parts of the device of FIG. 3.

A third device is depicted in FIGS. 3 and 4. The device 70 is cylindrical, having cylindrical membrane 72 fitted into cylinder 74 which serves as the membrane compartment. An inner tube or sleeve 76 serves for mounting the membrane 72 and to define the silicic acid compartment 80. Silicic acid particles 81 as described previously are then packed into silicic acid compartment 80. First and second screens 82 and 84 respectively are mounted at the bottom and top of compartment 80 to ensure that silicic acid particles do not escape.

The device may be assembled by employing top cap 85 and bottom cap 90 and mounting inner tube 76 on projection 86 which holds the inner tube 76 in place. Included within inner tube 76 is mounting 90 which includes conduit 92, which is in alignment with orifice 94 in innertube 76. Mounting 90 receives and holds first and second screens 82 and 84 in position to prevent the silicic acid particles 81 from entering the membrane compartment 74. The top cap 85 has plasma inlet 96 and plasma outlet 100.

After mounting the inner tube 76 on projection 86, membrane 72 is then fitted onto inner tube 76, followed by mounting of membrane compartment tube 74 which encloses membrane 72. Assemblage of the device is completed by adding the upper silicic acid screens 82 and 84 over the silicic acid, followed by enclosing the device with top cap 85 which includes plasma inlet orifice 96 and plasma outlet 100.

The top of the membrane may be coated with netting 102 which is held in place with a hot melt 104 so as to provide structural stability to the membrane 72.

In using the device, the plasma will enter inlet 96 and flow downwardly through membrane 72. The flow of plasma will be circular around the device, filling the membrane with the plasma. The plasma will reach the bottom of the device and pass through orifice 94 into conduit 92. From conduit 92, the plasma will pass through first and second screens 82 and 84 into the silicic acid particles 81, where anaphylatoxins will be removed. After passing upwardly through the silicic acid particles 81, the plasma will pass through upper screens 82 and 84 through outlet 100.

The membrane may then be easily removed for regeneration or other use by removing the top cap 85 and the membrane compartment 74 and retrieving the membrane 72 by removal from the sleeve or inner tube 76.

In many situations, it may be desirable to have a bag design, where the bag can be placed at bedside, conveniently hanging alongside of the bed, where blood can be removed from the patient, employing a pump, directed through the bag and returned to the patient. Such bags may find use during operations, during recovery, or in other situations where the patient requires some form of plasmapheresis.

In FIGS. 5 and 6 are depicted one type of bag assembly. The bag has housing 110, which includes at one end ring 112 for hanging. Within the bag is a first compartment 114, the membrane compartment, which has a membrane stack 116. The membrane stack 116 comprises outer sheets 120 which are conveniently polyvinylchloride, 0.015 inch thickness. Inside of the outer sheets 120 are screens 122 which serve to separate the membrane pack 124 from the outer sheets 120. Spacers 126 serve to hold the membrane pack in position and provide for maintenance of the various layers in appropriate spatial relationship.

A second compartment 130 serves as the silicic acid compartment. The housing 110 provides for the silicic acid compartment to be filled with silicic acid particles with screens at opposite ends to prevent the migration of silicic acid particles from the compartment. In addition, the two compartments are situated in parallel, so that the flow of plasma will be in opposite directions in the two compartments. As depicted, the flow of plasma enters inlet 132 and passes through the membrane pack 124. The plasma exits from the opposite end of the membrane pack 124 from which it entered and is connected by a tube, not shown, to the silicic acid compartment 130 where the plasma then passes through the silicic acid particles 134 and exits through outlet 136. A second ring 140 is provided, so that the bag housing 110 may be hung in either direction.

In the next embodiment, depicted in FIGS. 7 and 8, the device provides for a tortuous path, so as to substantially increase the membrane surface area and extend the contact time between the plasma stream and membranes. This device, which also provides for a bag, uses an accordian folding to provide for an extended path, while still requiring only a relatively small volume. The device 150 is folded so as to have a plurality of compartments 152 within housing 154. In each of the compartments 152 is a membrane pack 156. Between each compartment the housing turns providing a bend 160 in which is housed a spacer 162, which serves to regulate the rate of flow between the compartments 152. Inlet 164 and outlet 166 serve for ingress and egress of the plasma. Connected to outlet 166 is the silicic acid filter 170. The filter 170 has a tube connector 172, which connects to outlet 166. The silicic acid filter 170 is filled with silicic acid particles contained within screens, as depicted previously, to prevent the loss of particles through the silicic acid filter 170. Outlet 174 provides for the exiting of the plasma for subsequent use.

Other equipment may be employed with the device including additional extraction systems. Usually, a pump(s) will be employed to move the blood from the patient or other source through the various compartments and conduits. Various alarm and control systems may be employed for detecting rate of flow, flow blockages, air bubbles, clots or the like. Other components may be additional filters, adsorbents, chemical treatments, irradiation treatments, and the like.

The following examples are offered by way of illustration and not by way of limitation.

EXPERIMENTAL

To demonstrate the use of silicic acid for removing anaphylatoxins, the following examples were performed. Plasma was passed serially through a recombinant Protein A (rPA)-containing membrane pack, where the Protein A was covalently bonded to cellulose membranes employing sodium borohydride reduction of Schiff bases formed by reaction with aldehydes on the surface of the membrane with lysine amino groups of the Protein A.

Complement values were taken prior to introduction into the membrane compartment, post-membrane compartment and post-silicic acid treatment. The device employed 15 ft$^2$ of membrane area containing 750 mg of rPA. The membrane and silicic acid column were flushed in series with saline (0.9% 1 liter). It was found that a 71 gm column of silicic acid removed all anaphylatoxins generated by a 15 ft$^2$ device.

Membrane-silicic acid devices were devised where the inlet and outlet complement levels were determined for the membrane compartment. The effluent from the membrane compartment was then passed through a tube of silicic acid and the values determined again. The following tables indicates the results.

TABLE 1

| $C_{3a}$ and $C_{5a}$, 18 gm Silicic Acid Column In-Line with a 15 ft$^2$ Membrane Having 750 mg rPA* | | | |
|---|---|---|---|
| Time (minutes) | Inlet (ng/ml) | Outlet (ng/ml) | Post Silicic Acid (ng/ml) |
| (1) $C_{3a}$ and $C_{3a}$ des arg (ng/ml) Patient: LL Filter: Sil-A200 (18 gm) | | | |
| 0 | 640 | 660 | 704 |
| 10 | 428 | 13,440 | 204 |
| 20 | 428 | 24,320 | 480 |
| 30 | 420 | 24,460 | 572 |
| 45 | 344 | 22,400 | 1,260 |
| 60 | 380 | 25,280 | 1,400 |
| (2) $C_{5a}$ and $C_{5a}$ des arg (ng/ml) Patient: LL Filter: Sil-A200 (18 gm) | | | |
| 0 | 6 | 5 | 16 |

TABLE 1-continued

| $C_{3a}$ and $C_{5a}$, 18 gm Silicic Acid Column In-Line with a 15 ft$^2$ Membrane Having 750 mg rPA* | | | |
|---|---|---|---|
| Time (minutes) | Inlet (ng/ml) | Outlet (ng/ml) | Post Silicic Acid (ng/ml) |
| 10 | 4 | 235 | 76 |
| 20 | 4 | 536 | 248 |
| 30 | 4 | 608 | 288 |
| 45 | 4 | 592 | 372 |
| 60 | 4 | 560 | 320 |

*rPA = recombinant *S. aureus* Protein A

TABLE 2

| $C_{3a}$ and $C_{5a}$, 53 gm Silicic Acid Column In-Line with a 15 ft$^2$ Membrane Having 750 mg rPA | | | |
|---|---|---|---|
| Time (minutes) | Inlet (ng/ml) | Outlet (ng/ml) | Post Silicic Acid (ng/ml) |
| (1) $C_{3a}$ and $C_{3a}$ des arg (ng/ml) Patient: MM Filter: Sil-A200 | | | |
| 0 | 392 | 920 | 360 |
| 10 | 304 | 5,920 | 208 |
| 20 | 312 | 16,640 | 220 |
| 30 | 292 | 21,120 | 296 |
| 45 | 300 | 18,112 | 276 |
| 60 | 320 | 17,280 | 264 |
| (2) $C_{5a}$ and $C_{5a}$ des arg (ng/ml) Patient: MM Filter: Sil-A200 | | | |
| 0 | 4 | 12 | 20 |
| 10 | 4 | 272 | 29 |
| 20 | 4 | 544 | 96 |
| 30 | 4 | 736 | 208 |
| 45 | 4 | 832 | 248 |

The above results indicate the effect of varying amounts of silicic acid on the efficiency of removal of anaphylatoxins. The results demonstrate that the silicic acid can become saturated and further show the enhancement in the amount of anaphylatoxins when plasma is exposed to the membrane and other components in the first compartment.

Prototype devices were assembled comprising a first lower compartment with 10 ft$^2$ of membrane to which had been covalently bonded approximately 400 mg of recombinant Protein A and an upper compartment comprising 90 gm of silicic acid. High density polyethylene filters (35–60 $\mu$) were used to house the silicic acid. One device was employed without sterilization, while the other devices were employed with ethylene oxide sterilization. The following tables indicate the results.

TABLE 3

| Anaphylatoxin Generation, Assembled Device (Non-Sterilized), 10 ft$^2$, 400 mg rPA, 90 gm Silicic Acid | | |
|---|---|---|
| Time (minutes) | Inlet (ng/ml) | Outlet (ng/ml) |
| (1) $C_3$ and $C_{3a}$ des arg (ng/ml) | | |
| 0 | 276 | 1080 |
| 10 | 184 | 280 |
| 20 | 188 | 172 |
| 30 | 176 | 192 |
| 45 | 180 | 156 |
| 60 | 160 | 146 |
| (2) $C_{4a}$ and $C_{4a}$ des arg (ng/ml) | | |
| 0 | 516 | 862 |
| 10 | 210 | 174 |
| 20 | 205 | 152 |
| 30 | 176 | 114 |
| 45 | 216 | 101 |
| 60 | 161 | 93 |
| (3) $C_{5a}$ and $C_{5a}$ des arg (ng/ml) | | |

TABLE 3-continued

Anaphylatoxin Generation, Assembled Device (Non-Sterilized), 10 ft$^2$, 400 mg rPA, 90 gm Silicic Acid

| Time (minutes) | Inlet (ng/ml) | Outlet (ng/ml) |
|---|---|---|
| 0 | <4 | 42 |
| 10 | <4 | 21 |
| 20 | <4 | 48 |
| 30 | <4 | 84 |
| 45 | <4 | 88 |
| 60 | <4 | 104 |

TABLE 4

$C_{3a}$ and $C_{3a}$ des arg (ng/ml), Assembled Device Containing 90 gm Silicic Acid (ETO Sterilized)

| Time (minutes) | Inlet (ng/ml) | Outlet (ng/ml) |
|---|---|---|
| (1) Patient U (10 ft$^2$, 500 mg rPA, 90 gm silicic acid) | | |
| 0 | 212 | 1840 |
| 10 | 260 | 132 |
| 20 | 321 | 130 |
| 30 | 274 | 122 |
| 45 (40) | 243 | 146 |
| 60 (Procedure completed at 40 minutes) | | |
| (2) Patient S (10 ft$^2$, 500 mg rPA, 90 gm silicic acid) | | |
| 0 | 136 | 632 |
| 10 | 120 | 52 |
| 20 | 136 | 40 |
| 30 | 137 | 25 |
| 45 | 126 | 30 |
| 60 | 782 | 44 |
| (3) Patient T (10 ft$^2$, 500 mg rPA, 90 gm silicic acid) | | |
| 0 | 97 | 79 |
| 10 | 101 | 65 |
| 20 | 104 | 65 |
| 30 | 77 | 63 |
| 45 | 80 | 82 |
| 60 | 128 | 79 |

TABLE 5

$C_{4a}$ and $C_{4a}$ des arg (ng/ml), Assembled Device Containing 90 gm Silicic Acid (ETO Sterilized)

| Time (minutes) | Inlet (ng/ml) | Outlet (ng/ml) |
|---|---|---|
| (1) Patient S (10 ft$^2$, 400 mg rPA, 90 gm silicic acid) | | |
| 0 | 392 | 632 |
| 10 | 370 | 40 |
| 20 | 314 | 26 |
| 30 | 316 | 27 |
| 45 | 279 | 29 |
| 60 | 782 | 70 |
| (2) Patient T (10 ft$^2$, 400 mg rPA, 90 gm silicic acid) | | |
| 0 | 180 | 61 |
| 10 | 196 | 94 |
| 20 | 200 | 90 |
| 30 | 177 | 87 |
| 45 | 148 | 84 |
| 60 | 174 | 185 |
| (3) Patient U (10 ft$^2$, 400 mg rPA, 90 gm silicic acid) | | |
| 0 | 232 | 675 |
| 10 | 237 | 136 |
| 20 | 246 | 118 |
| 30 | 237 | 97 |
| 45 | 194 | 93 |
| 60 | | |

TABLE 6

$C_{5a}$ and $C_{5a}$ des arg (ng/ml), Assembled Device Containing 90 gm Silicic Acid (ETO Sterilized)

| Time (minutes) | Inlet (ng/ml) | Outlet (ng/ml) |
|---|---|---|
| (1) Patient S (10 ft$^2$, 400 mg rPA, 90 gm silicic acid) | | |
| 0 | <4 | 28 |
| 10 | <4 | <4 |
| 20 | <4 | <4 |
| 30 | <4 | 10 |
| 45 | 7 | 23 |
| 60 | 34 | 13 |
| (2) Patient U (10 ft$^2$, 400 mg rPA, 90 gm silicic acid) | | |
| 0 | <4 | 45 |
| 10 | <4 | 16 |
| 20 | <4 | 18 |
| 30 | <4 | 63 |
| 45 (40) | < | 77 |
| 60 (Procedure completed at 40 minutes) | | |
| (3) Patient T (10 ft$^2$, 400 mg rPA, 90 gm silicic acid) | | |
| 0 | <4 | 6 |
| 10 | <4 | 37 |
| 20 | <4 | 28 |
| 30 | <4 | 85 |
| 45 | <4 | 134 |
| 60 | <4 | 129 |

It is apparent from the above results that regardless of the plasma flow rate or volume of diffused plasma, the device adequately adsorbs $C_{3a}$, $C_{4a}$, $C_{5a}$ and $C_{3a}$-, $C_{4a}$- and $C_{5a}$ des arg, maintaining or reducing the inlet concentration.

Different silicic acids were tested to determine their relative effectiveness. The procedure employed was to weigh out 0.1 g dry weight of the particular silicic acid and add 4 ml plasma containing $C_{5a}$ to each in a 15 ml polypropylene tube. The tube was then shaken gently without bubble formation for 1 hour at 25° C., spun at 4200 rpm for 10 min and the plasma supernatant removed carefully. The plasma supernatant was then assayed for $C_{5a}$. The following table indicates the results.

TABLE 7

$C_5$ and $C_{5a}$ des arg Removal

| Silica Gel | | | | | $C_5$ and $C_{5a}$ des arg | | |
|---|---|---|---|---|---|---|---|
| Source | Designation | pH | Size ($\mu$) | Pore Size (Å) | Total ng/ml | ng[1] | % Depletion[2] |
| ICN | 03290-DCC | | | 100 | <7 | <28 | >98.9 |
| PQ | RG 1080 | 5 | 71 | 102 | <7 | <28 | >98.9 |
| PQ | RG 2080 | 5.2 | 74 | 191 | 27 | 107 | 95.7 |
| Aldrich | 23,683-9 | | 150–250 | 150 | 18 | 70 | 97.2 |
| Davisil | 644 | 7 | 90–130 | 150 | 18 | 72 | 97.6 |
| Davisil | 654 | 7 | 90–130 | 300 | 20 | 80 | 97.3 |

TABLE 7-continued

| | | | C$_5$ and C$_{5a}$ des arg Removal | | | |
|---|---|---|---|---|---|---|
| | Silica Gel | | | | C$_5$ and C$_{5a}$ des arg | |
| | | Size | Pore Size | Total | | % |
| Source | Designation pH | (μ) | (Å) | ng/ml | ng[1] | Depletion[2] |
| 3 | | | | 618–752 | 2470–3008 | 0/0 |

[1] Concentration × Volume.

[2] % Depletion = $\left( \dfrac{\text{Total ng control} - \text{Total ng sample}}{\text{Total ng control}} \right) \times 100.$

[3] Control.

In order to determine the specificity of the silicic acid, three devices comprising 10 ft$^2$ of membrane area with 400 mg of recombinant Protein A and 90 g of silicic acid sterilized with ethylene oxide were employed. Commonly measured serum chemistries were checked in afferent and efferent plasma. With the exception of dilutional changes secondary to the saline-/ACDA (acid-citrate dextran A) flush present in the system prior to plasma introduction, no significant changes were seen. The following table indicates the results

TABLE 8

Mean Values, Three (3) 10 ft$^2$ Devices, Each Containing 90 gm of Silicic Acid
(Average Flow Rate 40 ml/min)

| Serum Chemistry | 0 Minutes | | 10 Minutes | | 20 Minutes | | 30 Minutes | | 45 Minutes | |
|---|---|---|---|---|---|---|---|---|---|---|
| | Inlet | Outlet | Inlet | Outlet | Inlet | Outlet | Inlet | Outlet | Inlet | Outlet |
| Protein | 4.8 | 3.3 | 4.8 | 4.7 | 4.9 | 4.9 | 4.9 | 4.9 | 4.9 | 4.9 |
| Albumin | 3.3 | 2.6 | 3.3 | 3.2 | 3.5 | 3.4 | 3.7 | 3.5 | 3.8 | 3.5 |
| Sodium | 144 | 138 | 149 | 148 | 153 | 154 | 147 | 151 | 152 | 152 |
| Potassium | 3.0 | 1.4 | 3.0 | 2.6 | 3.2 | 2.9 | 3.3 | 3.1 | 3.3 | 3.2 |
| Chloride | 97 | 117 | 95 | 95 | 94 | 94 | 94 | 94 | 95 | 95 |
| BUN | 15 | 10 | 16 | 16 | 15 | 16 | 16 | 16 | 16 | 16 |
| Uric Acid | 4.8 | 2.7 | 3.6 | 3.5 | 3.5 | 3.1 | 3.0 | 3.6 | 3.4 | 3.0 |
| Calcium | 6.8 | 4.7 | 7.3 | 7.2 | 7.3 | 7.4 | 7.7 | 7.6 | 7.8 | 7.7 |
| Magnesium | 1.7 | 1.2 | 1.8 | 1.7 | 1.8 | 1.9 | 1.9 | 1.8 | 1.9 | 1.9 |
| Phosphorous | 2.5 | 1.6 | 2.7 | 2.5 | 2.5 | 2.7 | 2.6 | 2.6 | 2.5 | 2.6 |
| Total Bilirubin | 0.1 | 0.1 | 0.2 | 0.2 | 0.2 | 0.2 | 0.2 | 0.2 | 0.2 | 0.2 |
| SGOT | 6.6 | 5.0 | 6.0 | 6.0 | 5.6 | 5.3 | 4.7 | 5.3 | 4.3 | 4.3 |
| Alk. Phosphatase | 52.6 | 12.0 | 48.0 | 34.0 | 46.7 | 36.7 | 44.3 | 37.0 | 38.7 | 37.3 |
| LDH | 34 | 20 | 31.3 | 30.3 | 21 | 28 | 25.7 | 27 | 22.3 | 24 |
| Cholesterol | 136 | 108 | 124 | 123 | 109 | 113 | 100 | 103 | 85 | 90 |
| Tri-Glycerides | 144 | 169 | 152 | 153 | 125 | 150 | 117 | 134 | 109 | 118 |
| Glucose | 273 | 192 | 282 | 290 | 284 | 287 | 297 | 284 | 275 | 278 |
| CO$_2$ | 18.6 | 3.9 | 17.7 | 15 | 20 | 17 | 20 | 18 | 19.3 | 18.3 |
| Creatinine | 0.6 | 0.2 | 0.5 | 0.5 | 0.7 | 0.5 | 0.6 | 0.6 | 0.7 | 0.7 |

It is evident from the above results that the silicic acid component effectively removes anaphylatoxins while not altering the ion balance or other blood components normally present. Silicic acid can be used to effectively remove anaphylatoxins, while not adversely affecting other components normally found in plasma and serum. Thus, various techniques may be employed for removing components from blood to modify the blood for return to a host, without adversely affecting the anaphylatoxin level. In this way, blood can be treated without concern as to having any adverse affect on the patient.

All publications and patent applications mentioned in this specification are indicative of the level of skill of those skilled in the art to which this invention pertains. All publications and patent applications are herein incorporated by reference to the same extent as if each individual publication or patent application was specifically and individually indicated to be incorporated by reference.

Although the foregoing invention has been described in some detail by way of illustration and example for purposes of clarity of understanding, it will be obvious that certain changes and modifications may be practiced within the scope of the appended claims.

What is claimed is:

1. A method for reducing elevated levels of anaphylatoxins in a blood derived fluid consisting of serum or plasma having an initial level of at least one of the anaphylatoxins at least two times greater than the original blood level of anaphylatoxins comprising:
   contacting said fluid with an anaphylatoxin reducing amount of silicic acid.

2. A method according to claim 1, wherein said silicic acid is present in an amount of from about 10 to 100 g/L of fluid treated.

3. A method according to claim 1, wherein said silicic acid is characterized by having a pH in the range of about 4 to 7, a size in the range of about 50 to 400 μ, a pore size in the range of about 50 to 350 Å, and a surface area of at least about 200 m$^2$/g.

4. A method for treating blood to be administered to a mammalian host, said method comprising:
   preparing plasma from said blood;
   selectively changing the composition of said plasma by contacting said plasma with a membrane which specifically affects the composition of said plasma, whereby the level of anaphylatoxins may be increased; and
   contacting said plasma with silicic acid characterized by being capable of substantially selectively removing proteins having molecular weights in the range of about 15 to 50 kD and having a pI of greater than about 7, said silicic acid present in an amount sufficient to reduce the anaphylotoxins to at least substantially the original level of said plasma.

5. A method according to claim 4, wherein said membrane is an affinity membrane to which is covalently bonded a member of a specific binding pair homologous to said component.

6. A method according to claim 5, wherein said specific binding pair member is an antibody.

7. A method for treating a person to change the level of a blood component, said method comprising:
   removing blood from said person and separating plasma from said blood;
   selectively removing at least one component of said plasma by contacting said plasma with a membrane which specifically modifies the concentration of said component, whereby the level of anaphylatoxins may be increased; and
   contacting said plasma with silicic acid characterized by substantially selectively removing proteins having a molecular weight in the range of about 15 to 50 kD and a pI of greater than about 7, said silicic acid present in an amount sufficient to reduce the anaphylatoxins to at least substantially the original level of said plasma in said first compartment.

8. A method according to claim 7, wherein said silicic acid is characterized by having a pH in the range of about 4 to 7, pore size in the range of about 50 to 350 Å, an average particle size in the range of about 50 to 400 $\mu$, and a surface area of at least about 200 m$^2$/g.

* * * * *